United States Patent [19]
Grubhofer

[11] Patent Number: 6,004,564
[45] Date of Patent: *Dec. 21, 1999

[54] METHOD FOR INCREASING THE YIELD OF ANTIBODIES IN THE TECHNIQUES OF IMMUNOLOGY

[75] Inventor: Nikolaus Grubhofer, Gaiberg, Germany

[73] Assignee: Gerbu Biotechnik GmbH, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/542,643

[22] Filed: Oct. 13, 1995

Related U.S. Application Data

[63] Continuation-in-part of application No. 08/130,645, Oct. 1, 1993, abandoned.

[51] Int. Cl.[6] .......................... A61K 45/00; A61K 39/00; A61K 31/30; A61K 31/315
[52] U.S. Cl. .................................. 424/278.1; 424/184.1; 514/494; 514/499; 514/885; 530/388.1; 530/389.1
[58] Field of Search ..................................... 514/494, 499, 514/885; 424/184.1, 278.1; 530/388.1, 389.1

[56] References Cited

U.S. PATENT DOCUMENTS

| | | |
|---|---|---|
| 4,036,953 | 7/1977 | Adam et al. . |
| 4,082,735 | 4/1978 | Jones et al. . |
| 4,094,971 | 6/1978 | Chedid . |
| 4,395,399 | 7/1983 | Ovchinnikov . |
| 4,801,578 | 1/1989 | Monsiguy et al. . |
| 4,845,042 | 7/1989 | Newman et al. . |
| 4,877,612 | 10/1989 | Berger et al. . |
| 5,210,072 | 5/1993 | Chedid et al. . |
| 5,376,369 | 12/1994 | Allison et al. . |
| 5,773,011 | 6/1998 | Grubhofer . |

OTHER PUBLICATIONS

B. Bennett, et al (1992) "A comparison of commercially available adjuvants for use in research", in: Journal of Immunological Methods, vol. 153, pp. 31–40.
R. Bomford, et al (1992) "The Control of the Antibody Isotype Response to Recombinant Human Immunodeficiency Virus gp120 Antigen by Adjuvants", in : AIDS Research and Human Retroviruses, vol. 8, pp. 1765–1771.
F. Ellouz, et al (1974) "Minimal Structural Requirements for Adjuvant Activity of Bacterial Peptydoglycan Derivatives", in: Biochemical and Biophysical Research Communications, vol. 59, No. 4, pp. 1317–1325.
J. Freund, et al (1948) "Antibody Formation and Sensitization with the Aid of Adjuvants", in: J. Immunology, vol. 60, pp. 383–398.
T. Andronova, et al (1991) "The Structure and Immunomodulating Function of Glucosaminylmuramyl Peptides", in: Sov. Medical Reviews D Immunology, vol. 4, pp. 1–63.

Jules Freund, "The Mode of Action of Immunologic Adjuvants", in: Advances Tuberculosis Research, vol. 7, (1956) pp. 130–148.
H. Shaw Warren, et al, "Future Prospects for Vaccine Adjuvants", in: CRC Critical Reviews in Immunology, vol. 8, Issue 2 (1988), pp. 83–101.
Robert L. Hunter, et al, "The Adjuvant Activity of Nonionic Block Polymer Surfactants", in: The Journal of Immunology, vol 133, No. 6, Dec. 1984, pp. 3167–3175.
Anthony C. Allison, et al, "An adjuvant formulation that selectively elicits the formation of antibodies of protective isotypes and of cell–mediated immunity", in: Journal of Immunological Methods, vol. 95 (1986), pp. 157–168.
S. Kotani, et al, (1975) Biken J., vol. 18, pp. 105–111. Applicant does not presently have and has been unable to locate a copy of this reference; hence, no copy thereof is attached.
Masachika Tsujimoto, et al, "Adjuvant Activity of 6–0–Acyl–Muramyldipeptides to Enhance the Primary Cellular and Humoral Immune Responses in Guinea Pigs: Adaptability to Various Vehicles and Pyrogenicity", in: Infection and Immunity, Sep. 1986, pp. 511–516.
Noelene E. Byars, et al, "Adjuvant forumulation for use in vaccines to elicit both cell–mediated and humoral immunity", in: Vaccine, vol. 5, Sep. 1987, pp. 223–228.
Frederick R. Vogel, "A Compendium of Vaccine Adjuvants and Excipients", in: Vaccine Design, Pharmaceutical Biotechnology Series, Plenum Publishing Corporation, New York, NY (1994).
R. Bomford, "Adjuvants for Viral Vaccines", in: Reviews in Medical Virology, vol. 2, 1992, pp. 169–174.
Domkus et al. 1995 5th Int. Congress on Anti–Cancer Chemotherapy Poster P517.
Arakawa et al 1993. Adv. Drug Delivery Rev. 10:1–28.
Ramasamy et al. 1993. J. Natn. Sci. Council Sri Lanka 21(1):125–140.
Bahr et al 1983. Mol. Immunology 20(7):745–752.
Hosdorf et al 1935. J Immunologuy 29:389–425.
Nesmeyanov et al. 1990. Biomedical Sci. 1(2):151–154.
Shapira et al. 1985. Int. J. Immunopharmco. 7(5):719–723.
Grubhofer et al. 1994 FASEB Journal 8(4–5):A993.
Gregoriadis et al. 1989 Immunol Letters 20:237–240.
Shimizu et al 1992. Int. J. Immunopharmac. 14(8):1415–20.
Michalek et al 1983. Molecular Immunol 20(9):1009–18.
Sharma et al. 1988. Technol. Adv. Vaccine Dev. 107–116.

(List continued on next page.)

*Primary Examiner*—Nita Minnifield
*Attorney, Agent, or Firm*—Townsend and Townsend and Crew

[57] ABSTRACT

The new method uses synthetic glycopeptides such as MDP and GMDP as immunological adjuvants which according to this invention are added to the antigen in purely aqueous solution in the low doses discovered to evoke the maximum production of antibody output and whereby the adjuvant is present in dry form with L-proline added for better reproducibility of experiments by minimizing adsorptive losses at the walls of the glass vials.

8 Claims, 1 Drawing Sheet

OTHER PUBLICATIONS

Nash et al. 1985., J. Reprod. Immunol. 7:151–162.
Abehsira–Amar et al 1987. Mol. Immunol. 24(9):945–51.
Hilgers et al 1992. Res. Immunol. 143:494.
Isujimoto et al. 1986, Inf. & Imm. 53(3):511–516.
Allison et al 1988, Technol. Adv. Vaccine Dev. 401–409.
Mozes et al. 1980, PNAS 77(8):4933–4937.
Leclerc et al 1978, Immunology 35:963–970.
Léwy et al. 1980, Immunology 39:441–450.
Alam et al. 1991, Immunol. Letters 27:53–58.
Yin et al 1989, J. Biol. Response Modifiers 8:190–205.
Zhonghua Weishengwuxue He Mianyixue Zazhi Lu et al. 3(5):300–304 Abstract only, 1983.
Parant et al. Infection 13(Suppl 2):S251–S255, 1985.

METHOD FOR INCREASING THE YIELD OF ANTIBODIES IN THE TECHNIQUES OF IMMUNOLOGY

This application is a continuation-in-part application of U.S. Ser. No. 08/130,645, filed Oct. 1, 1993, for method for Increasing the Yield of Antibodies in the Techniques of Immunology, now abandoned.

This invention relates to improved methods for increasing the yield of antibodies in animals upon injection with antigens by using an admixture of the immunostimulating glycopeptides N-acetylmuramyl-L-alanyl-D-isoglutaminie. (MDP) and N-acetylglucosaminyl-N-acetylmuramyl-L-alanyl-D-isoglutamine (GMDP) in purely aqueous media and in very low doses.

BACKGROUND OF THE INVENTION

If an immune response is attempted in vertebrates including man by injecting antigens for the purpose of generating antibodies, be it for the protection of health by vaccination or for commercial use, the assistance of additives, called adjuvants, is often indispensable because in many cases the immune response is quite feeble.

DESCRIPTION OF PRIOR ART

Adjuvants for human use consist almost exclusively or a suspension of colloidal aluminium hydroxide. In animals the adjuvant is often the formulation invented by Jules Freund, a cream-like emulsion of paraffin synergistically combined with bacterial cell walls (J. Freund, K. Jefferson, Thompson, H. B. Hough, H. E. Sommer & T. M. Pisani (1948) J. Immunology 60, 383–98; J. Freund, (1956) Advances in Tuberculosis Research 7, 130–148). Freund's mixture is still commonly used in spite of severe drawbacks. The injected mineral oil can cause heavy and unsightly granulomas leading to the loss of animals. The bacterial material also contributes to undesirable side effects such as fever, granulomas, inflammations and arthritic symptoms. (H. S. Warren & L. A. Chedid (1988) CRC Critical Reviews in Immunology 8, 83–101). These effects also cause ethical reservations against the use of this adjuvant.

Many less toxic oil emulsions have been investigated, such as squalane or squalene emulsified with block polymers of polyethyleneglycol with polypropyleneglycol. (A. C. Allison & N. E. Byars (1986) J. Immunological Methods 95, 157–68, B. Bennet, I. J. Check, M. R. Olsen & R. L. Hunter (1992) J. of Immunological Methods 153, 31–40). These new oil emulsions are still reported to have adverse effects on the animals, such as fever and granulomas. There also remains the difficult task of properly and reproducibly preparing the emulsion from its various components.

In the intensive search for a replacement of the bacterial components (*Mycobacterium tuberculosis* or *M. butyricum*) it was found that low molecular weight glycopeptide subunits of the bacterial cell wall were about as effective as the native bacteria. N-dceLylmuramyl-L-alanyl-Du-isoglutamine (MDP) was the first of the compounds described. (P. Ellouz, A. Adam, R. Ciorbaru & E. Lederer (1974) Biochem. biophys. Res. Commun. 59, 1317–25;). More recently a glucosamine homolog of MDP, the N-acetylglucosaminyl-N-acetylmuramyl-L-alanyl-D-isoglutamine (GMDP), has been isolated from Lactobacillus bulgaricus and an efficient method of synthesis has been developed which makes this compound generally accessible. (V. Ivanov & T. Andronova (1991) Sovjet Medical Reviews, D. Immunology 4, 1–63 (R. V. Petrof, ed.), Harwood Academic Publishers; USSR Pat 2,543,268; U.S. Pat. No. 4,395, 399). GMDP has found considerable interest as a tumor inhibiting substance and has undergone extensive clinical and toxicological testing for this application.

The potential of MDP and GMDP as immunoadjuvants has been investigated. It has been demonstrated that doses of 100 µg per mouse given in aqueous solution are inactive (Chadid, L. Audibert, F, U.S. Pat. No. 4,094,971). The consensus is (R. Bomford, (1992) Reviews in Medical Virology 2, 169–74) that as adjuvants they only work together with oil emulsions and in the doses which are similar to the ones which are deemed necessary for the mycobactcria in Freund's adjuvant, and that only chemical modification of the native glycopeptides will make better immunoadjuvants out of them; (A. C. Allison & N. E. Byars, U.S. Pat. No. 5,217,493).

Attempts to modify MDP and GMDP do not appear to have produced generally accepted improved adjuvants. Furthermore, such modifications only increase the complexicity and cost of the materials.

Despite much work done over many years by many researchers, an objective analysis of research results available hitherto shows that even today Freund's complete adjuvant must be regarded as the best performing adjuvant available, at least prior to the present invention. However, Freund's complete adjuvant has substantial side effects which cause substantial distress to the animals and leads to a notably increased mortality rate.

PRINCIPAL OBJECT OF THE INVENTION

The principal object of the present invention is to provide an adjuvant which is at least of comparable efficiency to Freund's complete adjuvant, but which avoids the side effects associated therewith. The term "comparable efficiency" means, in the context of the present invention, an efficiency which is either as good as or better than Freund's complete adjuvant when comparing the respective yields of antibodies in particular animals using optimum doses in each cage, or an efficiency which is lower than that of Freund's complete adjuvant when comparing the respective yields of antibodies in a particular animal, but still an acceptable efficiency deemed useful in the art bearing in mind that fewer animals are lost, and that the animals are subjected to less distress.

A further object of the invention is to produce an adjuvant of an efficiency comparable to that of Freund's complete adjuvant, but available in a form easy to use at comparatively low cost and based on substances already known in the art per se.

A yet further object of the invention is to avoid unintentional wastage of the adjuvant.

Other aims and objects of the invention will become apparent from the further description.

SUMMARY OF THE INVENTION

The present invention is based on the discovery that, contrary to the findings of Bomford and of Chedid and Audibert as recited above, and contrary to expectation, MDP and GMDP are actually good adjuvants when used in quantities about 100 times smaller than before and in an aqueous solution rather than in an oil emulsion.

Thus this invention relates to improved methods for the use of the immunostimulating glycopeptides N-acetylmuramyl-L-alanyl-D-isoglutamine (MDP) and N-acetylglucosaminyl-N-acetylmuramyl-L-alanyl-D-isoglutamine (GMDP).

One aspect of the invention is a method for using MDP and GMDP in an aqueous solution, without, the need of an oil emulsion such as has commonly been used up to this time.

Another aspect of this invention is a method for the use of MDP and GMDP in concentrations that are lower than what has been used up to this time, surprisingly, large increases in immunostimulation were discovered as the adjuvant doses were decreased.

A further aspect of the invention is the use of a supplemental agent such as an amino acid which was found to decrease the loss of adjuvant due to adsorption onto the surfaces of the container, thereby increasing adjuvant effectiveness.

A final aspect of the invention is a method of preparing a lyophilized mixture of adjuvant components said lyophilized adjuvant formulation requiring only the addition of water in order to produce a complete adjuvant ready for injection or for further compounding.

DETAILED DESCRIPTION

Figure 1:
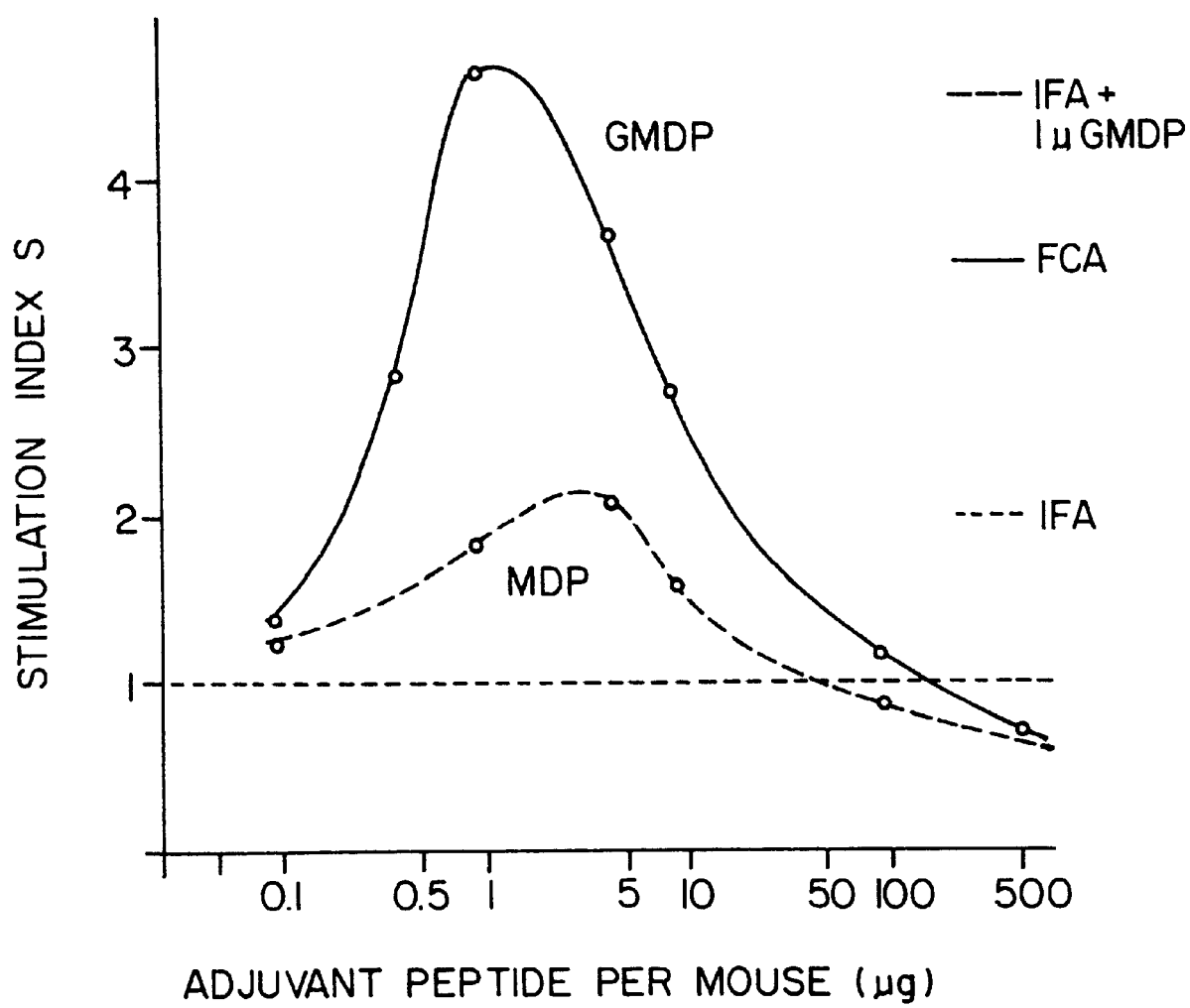
FIG. 1 shows the formation of antibodies in DNP-BSA in mice depending on dose of MDP and GMDP. The Y axis shows stimulation index and the X axis shows dose in micrograms.

On closer examination the various items of data available from the literature are quite conflicting. Many different authors, continents and decades apart from each other, have worked in different environments, with varying antigens, animals and methods. A great wealth of data has become available which however are sometimes quite contradictory and difficult to interpret in a synoptical way. Truly systematic, comparative studies are lacking. Therefore a preliminary study as an assessment of the present situation was a prerequisite for any methodical progress by further investigations.

Extensive immunisation studies have therefore been initiated and coherent, statistically relevant data have been obtained, prevalently with mice, but also with other animal species. Two types of antigens have been used for the tests reported here, namely the dinitrophenyl derivative of bovine serum albumin (DNP-BSA) and human lambda light chain (HILC), both giving very comparable results.

It is noted that it is a generally accepted finding that if an adjuvant is useful in promoting immune response with respect to one particular type of antigen it can also be expected to enhance immune response with other antigens.

The preliminary work can be summarized as follow:
1. In Freund's adjuvant the dogs of mycobacteria indeed give optimal results when added to the oil emulsion in the doses conventionally deemed necessary. Thus for mice 100 $\mu$g M. butyricum in one injection is best. If the doses are lowered, the effect decreases correspondingly as anyone would expect. (Table 1, expts. 3 and 4)
2. When the mycobacteria in Freund's adjuvant were replaced by MDP or GMDP in the analogous doses of 100 $\mu$g/mouse they give unimpressive results which confirm many findings in the literature that these glycopeptides indeed are immunostimulants, but rather inferior to M. tuberculosis or M. butyricum (FCA), (Table 1, expts. 5–7).

Based on the immunization studies just reported briefly, further investigation has lead to the simple and quite unexpected core of this invention: MDP and GMDP are quite good adjuvants, they just have been used the wrong way over the past 20 years of their existence.
3. Systematically lowering the doses of the glycopeptides actually results in greatly increased antibody outputs, eventually even surpassing those obtained with Freund's complete adjuvant (FCA). (Table 1, experiments 5, 6, 10–12).
4. There is clearly a dose-related optimum of efficacy for eliciting antibody formation in mice and other animals (Table 2, Drawing 1). However with animals other than mice, the glucopeptides even in optimum range were not as effective as Freund's adjuvant. The data are given in TABLE 3.
5. The optimum doses which were established are two orders of magnitude smaller than the quantity of mycobacteria deemed necessary to form good antibody yields with Freund's complete adjuvant.
6. In this low dose range, the antibody output with or without the oil emulsion is virtually the same, the emulsion becomes superfluous.
7. The research work also revealed the phenomenon of absorption of the glycopeptides into the walls of glass vials which casts doubt on the reliability of some of the earlier work in this field.

From the many tests carried out with mice, the results of the relevant ones to illustrate the newly discovered dose range effect of MDP and GMDP are shown in the accompanying drawing. The data used to produce the graph of the drawing comprises essentially the data shown in Table 1 supported by further experimental data.

With GMDP in water the optimum antibody output is 4.5 times higher than with water and 1.4 times higher than with Freund's complete adjuvant (FCA). Optimum dose range at 1 $\mu$g GMDP per mouse. With MDP in water the values were 1.8 times higher than with water and only 0.53 that with FCA. The optimum dose lies in both cases in the range 1–5 $\mu$g per mouse. Further experimental details are described later with reference to Table 1.

It will be noted from tho drawing that doses of MDP and GMDP above about 40 $\mu$g per mouse and 100$\mu$g per mouse respectively result in a stimulation index less than 1, i.e. less than what could be obtained with pure water! This confirms the findings of other workers in the field as explained above. Only with much lower concentrations of GMDP and MDP does the immune response reach values comparable with or better than those obtainable with Freund's complete adjuvant. It should be borne in mind that the abscissa in the drawing is to a logarithmic scale, so that the totally unexpected stimulation index peaks for both MDP and GMDP lie considerably further away from the doses previously investigated than the drawing tends to suggest. Thus, the drawing visually shows the optimum doses of MPD and GMDP for use on a mouse.

The form of a lyophilizate in serum vials was chosen as the method of making the adjuvant formulation available for practical use. In this case it would only be necessary to add the antigen solution in which the adjuvant material dissolves easily and the adjuvant would be ready to use. However it was found that apparently some of the glycopeptide is adsorbed on the surface of the glass container so that the expected effect had been reached only partially. This phenomenon contributed considerably to the initial experimental difficulties and quite possibly could be one of the reasons for contradictory data found in the literature. Eventually the problem was solved by the addition or physiologically inert amino acids, such as glycine, L-threonine or L-proline (Table 4). L-Proline was given preference and according to this invention is added to the GMDP in 100 fold weight excess. This additive has the additional benefit of giving volume to the otherwise invisible lyophilizate. Details see Example 3.

EXAMPLE 1

From the many experiments carried out a representative compilation is presented in Table 1, data have been obtained according to the protocol described above. The results are represented in comparative form as Stimulation index=titer of antibody obtained with adjuvant divided by titer of antibody in water only.

TABLE 1

Formation of Antibodies in Mice, depending on the adjuvants used and their doses.

| | Adjuvant | Dose μg | Stim. Ind. |
|---|---|---|---|
| 1 | None, (Antigen in water only) | | 1.00 |
| 2 | Freund's oil emulsion without *M. butyricum* (IFA) | — | 1.8 |
| 3 | Freund's oil elmusion, standard dose of *M. butyricum* (i.e. Freund's complete adjuvant) | 100 | 3.4 |
| 4 | Freund's oil emulsion, low *M. butyricum* | 10 | 1.9 |
| 5 | Freund's oil emulsion with GMDP | 100 | 1.6 |
| 6 | Freund's oil elmusion with GMDP | 10 | 2.3 |
| 7 | Freund's oil elmusion with GMDP | 1 | 4.2 |
| 8 | GMDP in water | 0.1 | 1.5 |
| 9 | GMDP in water | 0.5 | 3.7 |
| 10 | GMDP in water | 1.0 | 4.5 |
| 11 | GMDP in water | 5 | 3.7 |
| 12 | GMDP in water | 10 | 2.8 |
| 13 | GMDP in water | 100 | 1.3 |
| 14 | GMDP in water | 500 | 0.7 |
| 15 | MDP in water | 0.1 | 1.4 |
| 16 | MDP in water | 1 | 1.8 |
| 17 | MDP in water | 10 | 1.5 |
| 18 | MDP in water | 100 | 0.9 |

Entry 1 in the table sets the reference for adjuvant activity. In this case, the antigen (DNP-BSA) is injected into the mouse together with water and the resulting antibody titer is termed the stimulation index and given the reference value 1.00 for water.

Entry 2 in the table shows that if the antigen is injected mixed with Freund's oil emulsion, a substantially higher yield of antibodies is obtained since the stimulation index is 1.8, i.e. the antibody titer is 1.8 times higher than for water.

Entry 3 shows the most favourable value obtained with Freund's complete adjuvant including a standard dose of 100 μg of *M. butyricum*. The Stimulation index has the value of 3.4, i.e. 3.4 times the antibody titer is achieved when compared with water as used for entry 1.

Entry 4 shows that by reducing the dose of *M. butyricum* to 10 μg the stimulation index drops from 3.4 to 1.9, thus confirming the expectations of persons skilled in the art that a reduction in the dose from the optimum of 100 μg per mouse leads to inferior results.

Entry 5 thens shows the result of substituting 100 μg of GMPD for the 100 μg of *M. butyricum* entry number 3. Here, the stimulation index is 1.6, i.e. it is less than half that for *M. butyricum* and 0.2 less than the value or entry 2 for Freund's oil emulsion without *M. butyricum*. This entry thus confirms previous findings in the art that GMDP in a standard dose or 100 μg per mouse is ineffective. I.e., the person skilled in the art would have no reason to investigate GMDP further. If he did so, then, using conventional reasoning, he would increase the dose and would find no improvement. Hence, there would be no incentive to further investigate GMDP, which is borne out by the fact that researchers in the field then tried modified versions of GMDP (U.S. Pat. No. 5,219,493) which do not appear to have been successful.

Contrary to conventional wisdom, experiments were then conducted with lower doses of GMDP in Freund's oil emulsion. A reduction to 10 μg GMPD per mouse resulted in an increase of the stimulation index to 2.3 (entry 6) and a further reduction to 1 μg per mouse resulted in a surprisingly high stimulation index of 4.2, already notably higher than the best value of 3.4 for the stimulation index for Freund's complete adjuvant (entry 3).

Despite the findings by Chedid and Audibert (U.S. Pat. No. 4,094,471) that a dose of 100 μg of GMDP in water is ineffective as an adjuvant, borne out by entry 14 of Table 1, an investigation was made with lower doses of GMDP in an aqueous solution. As can be seen from entry 11, a reduction to 1.0 μg GMDP in aqueous solution resulted in the best value for the stimulation index of 4.5 which is better still than the value of 4.2 for 1.0 μg GMDP in Freund's oil emulsion (entry 7).

Entries 8 and 9 show that still lower doses of 0.1 μg and 0.5 μg GMDP yield poorer results as do higher doses or 5 μg and 10 μg (entries 11 and 12) and as does a much higher dose still of 500 μg GMDP (entry 14).

The stimulation index of 3.7 for entry 11 with 5 μg GMDP is still a respectable value. However, it will be appreciated that it is more coat effective to use a dose ⅕ of the size and to achieve a 20% higher yield of antibodies as documented by entry 10 in comparison to entry 11. Moreover, the truly surprising discovery is that in low doses the GMDP is effective in an aqueous solution, i.e. the oil emulsion is unnecessary. This is a substantial breakthrough, since the oil emulsion causes undesirable side effects not found with the aqueous solution, and since the preparation of the aqueous solution is much easier than the preparation of the oil emulsion. Not only this, but the yield of antibodies with an optimum dose of GMDP in aqueous solution is even higher than the best value previously obtained, as can be seen from a comparison of the stimulation index of 4.5 for entry 10 in comparison to 4.2 for entry 7.

Entries 15 to 18 show a similar pattern to that of entries 8 to 14, but using MDP in an aqueous solution in place of GMDP in aqueous solution.

The best value for MDP is the stimulation index or 1.8 for a small dose of 1.0 μg per mouse. Although this value for the stimulation index may not strike one as being particularly impressive on first inspection, in must be understood that the yield of antibodies is enhanced with MDP without side effects and without an increase in the mortality rate of the mice when compared with the use of oil emulsions. This compensates for the relatively lower stimulation index, particularly when the ease of preparation and the relative costs are considered.

In all the above tests adjuvants were tested by injecting them into mice along with the antigens and the developing antibodies are assayed. One single injection was applied to one single site subcutaneously, a second injection with antigen and adjuvant was applied after 21 days. With both antigens 1 μg per mouse was better than Freund's complete adjuvant.

A typical protocol showing antibody titers for two Antigens is shown in Table 2, the titers here are given in absolute dilution numbers.

TABLE 2

Formation of antibodies in mice using 10 μg DNP-BSA and Human lambda Light Chain antigens

| Experiment | Day 21 | Day 42 | Day 54 | Day 64 | Day 54 |
|---|---|---|---|---|---|
| 1 Control: DNP-BSA without adjuvant | 2 | 153 | | 1920 | 1338 |
| 2 DNP-BSA Freund's complete adjuvant | 21 | 574 | | 6600 | 2682 |
| 3 DNP-BSA 1 μg GMDP/mouse | 28 | 702 | | 8640 | 4230 |
| 4 Control: Human lambda LC w/o adjuvant | | 250 | 1600 | | |
| 5 Human lambda LC, Freund's complete | 1200 | 4500 | 6700 | | |
| 6 Human lambda LC, 1 μg GMDP/mouse | 1400 | 7500 | 42000 | | |

The experimental parameters for the tests on which Table 2 are based were as follows: Immunization at day 0 and a boost at day 21. Mice: female C3H strain, groups of five, serum preparation: Bleeds were placed in micro tubes, allowed to clot, centrifuged. The serum was removed for assay. Antigens: Human lambda Light Chain (Human lambda LC) and Dinitrophenyl-Bovine serum albumine (DNP-BSA) were obtained from Sigma chemical Company St. Louis Mo. MDP was obtained from Shemiakin Institute in Moskow, GMDP was produced by Peptech Inc. 60 Dyer Street, Cirencester Glos GL7 2PF UK under license from Shemiakin Institute. ELISA protocol: 5 μg of antigen was coated in each well. The blocking agent was skim milk. 1 hr serum incubation—1 hr detecting antibody—1 hr color development. The titer was measured as dilution necessary to reach standard colour appearing with 1 μg antibody per ml.

Entry 1 shows the development of antibodies in a mouse to the antigen DNP-BSA without an adjuvant. It will be noted that the highest antibody titer was 1920 achieved on day 64.

Using Freund's complete adjuvant with the same quantity of the same antigen (10 μg) the best result is again obtained on day 64 and has a value of 6600, i.e. some 3.4 times better than for entry 1.

Entry 3 shows the results obtained with 1 μg GMDP in an aqueous solution with the DNP-BSA antigen. It is notable that the value of 8640 for the antibody titer after 64 days compares very favourably to the best value of 6600 for Freund's complete adjuvant, particularly bearing in mind the absence of side effects.

Entry 4 shows another control similar to entry 1, but using human lambda LC antigen, again without an adjuvant. The antibody titer is again relatively low having reached a value of 1600 after 54 days.

Entry 5 shows the relatively better performance using Freund's complete adjuvant, where a maximum antibody titer of 6700 was obtained at 54 days.

Entry 6 shows the use of 1 μg of GMDP in aqueous solution as an adjuvant with the human lambda LC antigen. Here, the antibody titer has a maximum value of 42000 after 54 days compared with 1600 for the antiqen alone and 6700 for Freund's complete adjuvant. This is a spectacular improvement. This table incidently confirms that the data of Table 1 obtained using the antigen DNP-BSA also read over to another antigen, namely the human lambda LC antigen.

EXAMPLE 2

In order to test the general nature of the findings with mice, some preliminary tests were performed with other animal species. The resulting data are summarized in Table 3, showing that there was definitely an adjuvant effect also with other species, but the most favourable results when compared with Freund's adjuvant were obtained in mice.

The antigen was DNP-BSA, the titer measured after 64 days. With hens also after 26–30 days where titers relative to Freund's adjuvant were approx 30% higher than after 64 days.

Other experimental conditions as in Example 1. With the hens, eggs of days 26–30 and days 60–66 were pooled. The IgY contained in the yolk of the eggs was enriched for ELISA test by the method of J. Wallmann, C. Staak & E. Luge (1990) J. Vet. Med. B37, 317–20.

TABLE 3

Characteristic Dose Ranges of GMDP for obtaining Maximum Antibody Output in various Animals

| | Optimum Dose for maximal Immune Response | | Stimulation Index at Optimum Range compared with Injection, w/o Adjuvant | | Relative Antibody titer at Optimum Range compared with Freund's Adjuvant |
|---|---|---|---|---|---|
| | Range | Actual | | | |
| Mouse | 0.5–5 μg | 1 μg | 4.5 | | 1.3 |
| Hen | 1–10 μg | 5 μg | 2.0 | 1.6 (day 28) | 0.6 | 0.8 |
| Rabbit | 10–50 μg | 20 μg | 1.6 | | 0.4 |
| Sheep/Goat | 25–100 μg | 50 μg | 1.4 | | 0.1 |

Although the adjuvant effect in animals larger than mice seems to drop off with increasing size of the animals, it will be noted that, for example, the 0.8 value for hens for the relative antibody titer at optimum range compared with Freund's adjuvant is still a respectable value having regard to the avoidance of distress to the animals and the lower mortality rate.

EXAMPLE 3

It has been noted above that a phenomenon discovered in the course of work leading to the present application is the apparent adsorption of GMDP on the glass wall of serum vials. It has also been found that this GMDP is apparently desorbed by a 100-fold weight excess of common amino acids. This is shown by Table 4 with reference to comparative experimental results, i.e. antibody titers with and without an excess of amino acid.

TABLE 4

Apparent antibody titers upon injection of adjuvant formulations dissolved in aqueous BSA solutions depending on amino acid additives

| 4 Group of mice (number each) | I | II | III |
|---|---|---|---|
| 1) 1 μg GMDP alone without additive | 2.1 (10) | 3.0 (9) | 1.9 (10) |
| 2) 1 μg GMDP + 0.1 mg L-Proline | 4.9 (5) | 4.4 (10) | 5.1 (10) |
| 3) 1 μg GMDP + 0.1 mg L-Threonine | 4.7 (5) | | |
| 4) 1 μg GMDP + 0.1 mg Glycine | 3.8 (5) | | |

It will first be noted that three different groups of mice were used for the tests of each of the lines 1 and 2, hence three columns I, II, III, whereas just one group was used for the tests underlying the entries of lines 3 and 4. In each case the number of mice in each group is shown in brackets. The number before the brackets is in each case the stimulation index measured for the pooled serum in the manner previously described for example 1. It will be noted that it is very difficult to accurately dispense 1 μg of GMDP because of the very small volume. Thus, larger quantities of GMDP were used and were diluted in water. It is then possible to draw off larger volumes of the diluted solution which contain the desired dose of GMDP, i.e. 1 μg per mouse.

The values of 1 μg GMDP and 0.1 mg for the amino acid shown in Table 4 were obtained in this way. More specifically, the samples were prepared basically as follows using the examples of the entry of line 2.

100 μg GMDP 20 mg amino acid L-Proline contained in 100 μl water were pipetted into 5 ml serum vials of glass, hydrolytic class 1, manufactured by Müller GmbH. In Experimental series III, the solvent was 96% ethanol which was evaporated in a desicoator over sulfuric acid without vacuum. Other experimental details see Example 1.

It can be seen from Table 4 that when using 1 μg of GMDP alone, stimulation indioce of 2.1, 3.0 and 1.9 are obtained for the groups I, II, and III respectively. When 100 times as much L-Proline is added, the stimulation index increases to 4.9, 4.4 and 5.1 respectively. This is interpreted to mean that some of the GMDP has been lost in the experiments of line 1 by adsorption into the wall of the glass vial and has been desorped by the excess of amino acid in the experiments of lines 2, 3 and 4 of Table 4. Lines 3 and 4 of Table 4 show that amino acids other than L-Proline have the same effect. It is noted that the addition of the amino acid has the beneficial side effect that it adds volume to the microscopic amount of GMDP in a vial so that the customer or user does not think he has an empty vial when adding water or water and antigen to prepare an injection for the animal concerned. It is particularly beneficial that a standard dose is available as a lyophilizate in a glass vial which only needs the addition of water or aqueous antigen solution to yield the injectable liquid dose or dose 5.

I claim:

1. A method for increasing the yield of antibodies in animal by injecting a fluid composition comprising an adjuvant and an antigen, wherein said adjuvant is a glycopeptide and said glycopeptide is used in a dose optimal for the production of antibodies in a given animal species and wherein said adjuvant is presented in the form of a solid adjuvant formulation to which an aqueous solution of the antigen is added thereby dissolving said adjuvant formulation and forming a finished injection fluid without the formation of an oil emulsion wherein said adjuvant is not conjugated to said antigen and wherein said optimal dose is about 100 times smaller than an effective dose of said glycopeptide in an oil-based emulsion.

2. The method as claimed in claim 1, wherein said glycopeptide is N-acetylmuramyl-L-alanyl-D-isoglutamine (MDP).

3. The method as claimed in claim 1, wherein said glycopeptide is N-acetylglucosaminyl-N-acetylmuramyl-L-alanyl-D-isoglutamine (GMPD).

4. The method as claimed in claim 1, wherein an amino acid selected from the group consisting of glycine or L-proline in included in the mixture in order to reduce adsorption of adjuvant or antigen onto the walls of the vessel.

5. The method as claimed in claim 1, wherein said dose is 0.5–5 μg GMDP for mice.

6. The method as claimed in claim 1, wherein said dose is 1–10 μg GMDP for hens.

7. The method as claimed in claim 1, wherein said dose is 10–50 μg GMDP for rabbits.

8. The method as claimed in claim 1, wherein said dose is 50–100 μg GMDP for goats or sheep.

* * * * *